United States Patent
Yadin

(10) Patent No.: US 11,501,873 B2
(45) Date of Patent: Nov. 15, 2022

(54) PREDICTIVE VISUALIZATION FOR AESTHETIC MEDICAL PROCEDURES

(71) Applicant: EntityMed, Herzliya (IL)

(72) Inventor: Lior Yadin, Herzliya (IL)

(73) Assignee: EntityMed, Herzliya (IL)

( * ) Notice: Subject to any disclaimer, the term of this patent is extended or adjusted under 35 U.S.C. 154(b) by 0 days.

(21) Appl. No.: 17/698,883

(22) Filed: Mar. 18, 2022

(65) Prior Publication Data

US 2022/0301692 A1 Sep. 22, 2022

Related U.S. Application Data

(60) Provisional application No. 63/163,431, filed on Mar. 19, 2021.

(51) Int. Cl.
| | | |
|---|---|---|
| *G16H 30/40* | (2018.01) | |
| *G16H 50/20* | (2018.01) | |
| *A61B 34/10* | (2016.01) | |

(52) U.S. Cl.
CPC ............. *G16H 30/40* (2018.01); *A61B 34/10* (2016.02); *G16H 50/20* (2018.01)

(58) Field of Classification Search
CPC ......... G16H 30/40; G16H 50/20; A61B 34/10
See application file for complete search history.

(56) References Cited

U.S. PATENT DOCUMENTS

| | | | | |
|---|---|---|---|---|
| 11,123,140 B1 * | 9/2021 | Sweis | ..................... | A61B 34/10 |
| 2011/0270588 A1 * | 11/2011 | Kuo | ....................... | G16H 50/50 |
| | | | | 703/2 |
| 2011/0288890 A1 | 11/2011 | Dalton et al. | | |
| 2014/0279746 A1 | 9/2014 | De Bruin et al. | | |
| 2014/0304629 A1 * | 10/2014 | Cummins | .............. | A61B 5/742 |
| | | | | 715/764 |
| 2016/0378919 A1 | 12/2016 | McNutt et al. | | |
| 2017/0020610 A1 * | 1/2017 | Slayton | ............... | G06F 3/04842 |
| 2019/0130792 A1 * | 5/2019 | Rios | ..................... | G09B 23/285 |

(Continued)

OTHER PUBLICATIONS

Ali Shah et al., "A Fully Automatic Framework for Prediction of 3D Facial Rejuvenation", 2018 International Conference on Image and Vision Computing New Zealand (IVCNZ), 2018, pp. 1-6 (Year: 2018).*

(Continued)

*Primary Examiner* — Nay A Maung
*Assistant Examiner* — Jose M Torres
(74) *Attorney, Agent, or Firm* — Greenberg Traurig, LLP

(57) ABSTRACT

A method includes training a machine learning model to generate predicted images to obtain a trained machine learning model, based on: a) pre-treatment training images; b) a plan of treatment; and c) post-treatment training images; where the plan of treatment includes: a) a first mark identifying where to apply a product, b) a first product to be applied at the first mark, and c) a first volume of the first product to be applied at the first mark; generating a predicted post-treatment image by applying the trained predictive visualization machine learning model to a new pre-treatment image, based on: a) a second mark on a new pre-treatment image of the area of a patient, b) a second product to be applied at the second mark, and c) a second volume of the second product to be applied at the second mark; where the predicted images identifies a modified area.

10 Claims, 13 Drawing Sheets

(56) References Cited

U.S. PATENT DOCUMENTS

2019/0251723 A1    8/2019    Coppersmith, III et al.
2020/0054216 A1    2/2020    Cheng et al.
2020/0365268 A1    11/2020    Michuda et al.

OTHER PUBLICATIONS

International Search Report and Written Opinion from International Application No. PCT/IB2022/000142 dated Jul. 20, 2022.
Craft et al. "An Assessment of Visualization Tools for Patient Monitoring and Medical Decision Making", IEEE Systems and Information Engineering Design Symposium, 2015.

* cited by examiner

250

PREDICTIVE VISUALIZATION FOR AESTHETIC MEDICAL PROCEDURES

FIELD

The present disclosure relates generally to enhanced predictive visualization systems and platforms for providing modified predictive images and live three-dimensional video for medical procedures. Specifically, the present disclosure relates to artificial-intelligence enhanced predictive visualization of aesthetic medical procedures and platforms for displaying such predictive visualization.

BACKGROUND

Aesthetic or cosmetic procedures are a quickly growing field of medicine. Aesthetic procedures may be invasive or non-invasive. For example, two popular aesthetic procedures ae injections of neuromodulators, such as Botox®, and dermal fillers, such as Restylane®. The methods of administering injections typically vary for different procedures and may depend on the substance being injected, the needle size, or the area of injection. In some instances, these aesthetic procedures can alter the appearance of the treated part of the patient. The providers of such aesthetic procedures include, for example, plastic surgeons, dermatologists, physician assistants, nurse practitioners, dentists and nurses.

SUMMARY

The summary is a high-level overview of various aspects of the invention and introduces some of the concepts that are further detailed in the Detailed Description section below. This summary is not intended to identify key or essential features of the claimed subject matter, nor is it intended to be used in isolation to determine the scope of the claimed subject matter. The subject matter should be understood by reference to the appropriate portions of the entire specification, any or all drawings, and each claim.

In some embodiments, the present disclosure provides an exemplary technically improved computer-based method that includes training, by a processor, a predictive visualization machine learning model to generate predicted post-treatment images to obtain a trained predictive visualization machine learning model, based at least in part on: a) a set of pre-treatment training images of at least one area of a human; b) a plan of treatment related to the set of pre-treatment training images; and c) a set of post-treatment training images of the at least one area of the human related to the pre-treatment training images and the plan of treatment; where the plan of treatment includes: a) at least one first treatment mark identifying where a product is to be applied on a pre-treatment image, b) a first product to be applied at the at least one treatment mark, and c) a first volume of the product to be applied at the at least one treatment mark; generating, by the processor, at least one predicted post-treatment image by applying the trained predictive visualization machine learning model to at least one new pre-treatment image, based at least in part on a new plan of treatment including: a) at least one second treatment mark on a new pre-treatment image of the at least one area of a patient, b) a second product to be applied at the at least one second treatment mark, and c) a second volume of the second product to be applied at the at least one second treatment mark; where the at least one predicted post-treatment image identifies at least one modified area; and instructing, by the processor, to display the at least one predicted post-treatment image on a screen.

In some embodiments, the present disclosure provides the exemplary technically improved computer-based methods that further include receiving, by the processor, from the patient: a) at least one patient image; and b) at least one patient treatment request; where the new plan of treatment is based at least in part on the at least one patient image and the at least one patient treatment request.

In some embodiments, the present disclosure provides the exemplary technically improved computer-based methods where the machine learning model includes one or more of a neural network, a radial basis function network, an image classifier, a recurrent neural network, a convolutional network, a generative adversarial network, a fully connected neural network, a feedforward neural network, or a combination thereof.

In some embodiments, the present disclosure provides the exemplary technically improved computer-based methods where the machine learning model applies at least one loss function to the post-treatment training images.

In some embodiments, the present disclosure provides the exemplary technically improved computer-based methods where the at least one loss function comprises a mean square error loss function, an internal adversarial network, an opensource adversarial network, or a combination thereof.

In some embodiments, the present disclosure provides the exemplary technically improved computer-based methods where the first product comprises at least one of a prescription injection or a dermal filler.

In some embodiments, the present disclosure provides the exemplary technically improved computer-based methods where the second product is the same as the first product.

In some embodiments, the present disclosure provides the exemplary technically improved computer-based methods where the machine learning model is trained on thousands of pre-treatment training images and post-treatment training images.

In some embodiments, the present disclosure provides the exemplary technically improved computer-based methods that further include applying, by the processor, a registration process to finetune the alignment of the pre-treatment training images with the alignment of the post-treatment training images.

In some embodiments, the present disclosure provides the exemplary technically improved computer-based methods where the registration process identifies from 10 to 500 facial landmarks on the pre-treatment training images and the post-treatment training images.

BRIEF DESCRIPTION OF THE FIGURES

The accompanying drawings are included to provide a further understanding of the disclosure and are incorporated in and constitute a part of this specification, illustrate embodiments, and together with the description serve to explain the principles of the present disclosure.

DETAILED DESCRIPTION

Figure 1:
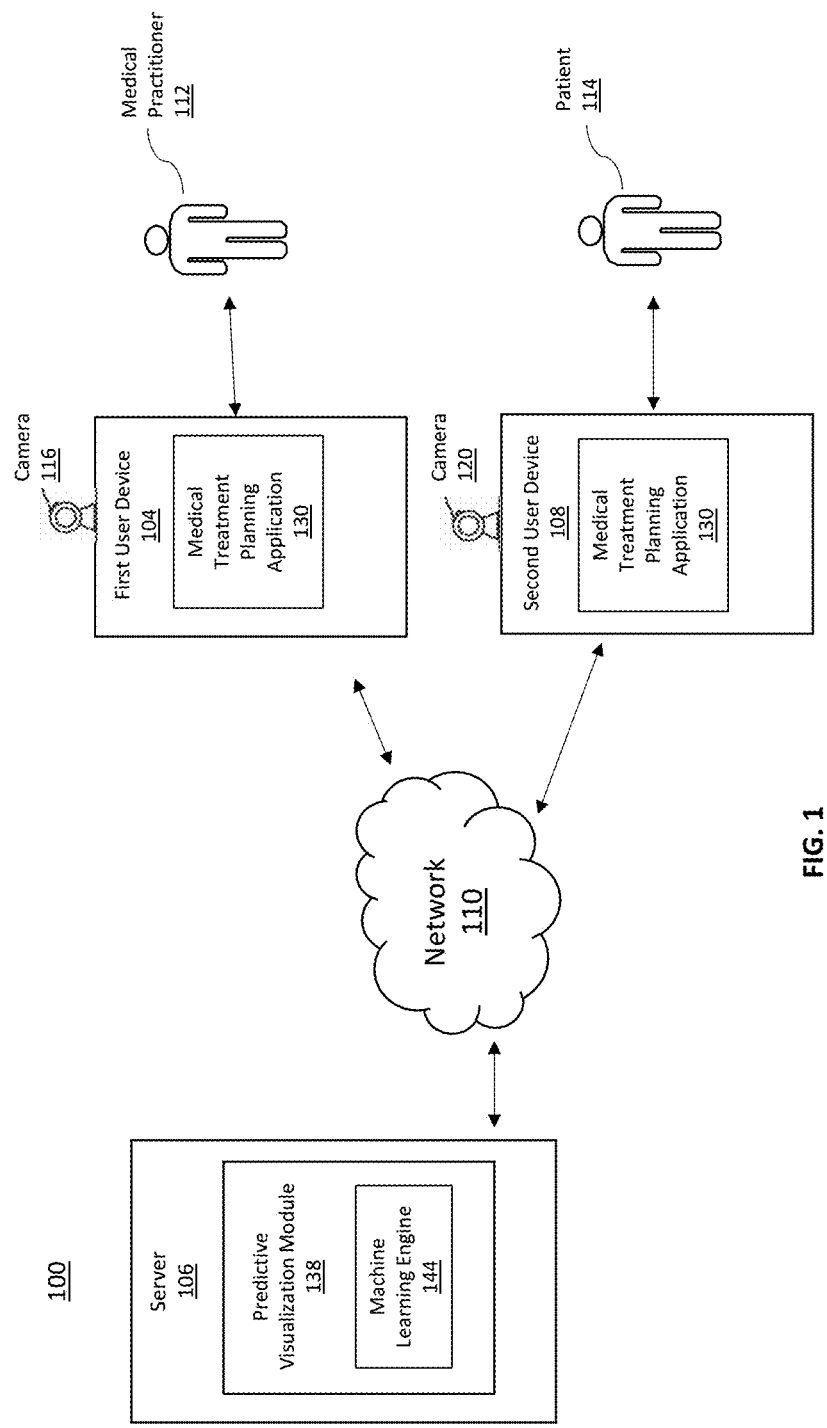
FIG. 1 is a block diagram illustrating an operating computer architecture for predictive visualization of a medical procedure of a patient, according to one or more embodiments of the present disclosure.

The present invention can be further explained with reference to the included drawings, wherein like structures are referred to by like numerals throughout the several views. The drawings shown are not necessarily to scale, with emphasis instead generally being placed upon illustrating the principles of the present invention. Therefore, specific structural and functional details disclosed herein are not to be interpreted as limiting, but merely as a representative basis for teaching one skilled in the art to variously employ the present invention.

Among those benefits and improvements that have been disclosed, other objects and advantages of this invention can become apparent from the following description taken in conjunction with the accompanying figures. Detailed embodiments of the present invention are disclosed herein; however, it is to be understood that the disclosed embodiments are merely illustrative of the invention that may be embodied in various forms. In addition, each of the examples given in connection with the various embodiments of the present invention is intended to be illustrative, and not restrictive.

Described herein are systems and methods for providing enhanced predictive images for aesthetic medical procedures. Also described herein are platforms for providing such enhanced predictive images. In some embodiments, artificial intelligence (AI) is used to optimize the predictive images provided by the platform.

In some embodiments, as described above, AI is used to produce a predictive image as a result of various inputs or parameters. In some embodiments, the AI includes at least one machine learning model, such as a neural network. In some embodiments, the neural network is a convolutional neural network. In other embodiments, the neural network is a deep learning network, a generative adversarial network, a recurrent neural network, a fully connected network, or combinations thereof.

Throughout the specification, the following terms take the meanings explicitly associated herein, unless the context clearly dictates otherwise. The phrases "in one embodiment" and "in some embodiments" as used herein do not necessarily refer to the same embodiment(s), though it may. Furthermore, the phrases "in another embodiment" and "in some other embodiments" as used herein do not necessarily refer to a different embodiment, although it may. Thus, as described below, various embodiments of the invention may be readily combined, without departing from the scope or spirit of the invention. Further, when a particular feature, structure, or characteristic is described in connection with an implementation, it is submitted that it is within the knowledge of one skilled in the art to effect such feature, structure, or characteristic in connection with other implementations whether or not explicitly described herein.

In addition, as used herein, the term "or" is an inclusive "or" operator, and is equivalent to the term "and/or," unless the context clearly dictates otherwise. The term "based on" is not exclusive and allows for being based on additional factors not described, unless the context clearly dictates otherwise. In addition, throughout the specification, the meaning of "a," "an," and "the" include plural references. The meaning of "in" includes "in" and "on."

It is understood that at least one aspect/functionality of various embodiments described herein can be performed in real-time and/or dynamically. As used herein, the term "real-time" is directed to an event/action that can occur instantaneously or almost instantaneously in time when another event/action has occurred. For example, the "real-time processing," "real-time computation," and "real-time execution" all pertain to the performance of a computation during the actual time that the related physical process (e.g., a user interacting with an application on a mobile device) occurs, in order that results of the computation can be used in guiding the physical process.

As used herein, the term "dynamically" means that events and/or actions can be triggered and/or occur without any human intervention. In some embodiments, events and/or actions in accordance with the present invention can be in real-time and/or based on a predetermined periodicity of at least one of: nanosecond, several nanoseconds, millisecond, several milliseconds, second, several seconds, minute, several minutes, hourly, several hours, daily, several days, weekly, monthly, etc.

In some embodiments, the inventive specially programmed computing systems with associated devices are configured to operate in the distributed network environment, communicating over a suitable data communication network (e.g., the Internet, etc.) and utilizing at least one suitable data communication protocol (e.g., IPX/SPX, X.25, AX.25, AppleTalk™, TCP/IP (e.g., HTTP), etc.). Of note, the embodiments described herein may, of course, be implemented using any appropriate hardware and/or computing software languages. In this regard, those of ordinary skill in the art are well versed in the type of computer hardware that may be used, the type of computer programming techniques that may be used (e.g., object oriented programming), and the type of computer programming languages that may be used (e.g., C++, Objective-C, Swift, Java, Javascript). The aforementioned examples are, of course, illustrative and not restrictive.

As used herein, the terms "image(s)", "image data" and "visual data" are used interchangeably to identify data representative of visual content which includes, but not limited to, images encoded in various computer formats (e.g., ".jpg", ".bmp," etc.), streaming video based on various protocols (e.g., Real-time Streaming Protocol (RTSP), Real-time Transport Protocol (RTP), Real-time Transport Control Protocol (RTCP), etc.), recorded/generated non-streaming video of various formats (e.g., ".mov," ".mpg," ".wmv," ".avi," ".flv," etc.), and real-time visual imagery acquired through a camera application on a mobile device.

As used herein, term "server" should be understood to refer to a service point which provides processing, database, and communication facilities. By way of example, and not limitation, the term "server" can refer to a single, physical processor with associated communications and data storage and database facilities, or it can refer to a networked or clustered complex of processors and associated network and storage devices, as well as operating software and one or more database systems and application software that support the services provided by the server. Cloud servers are examples.

The material disclosed herein may be implemented in software or firmware or a combination of them or as instructions stored on a machine-readable medium, which may be read and executed by one or more processors. A machine-readable medium may include any medium and/or mechanism for storing or transmitting information in a form readable by a machine (e.g., a computing device). For example, a machine-readable medium may include read only memory (ROM); random access memory (RAM); magnetic disk storage media; optical storage media; flash memory devices; electrical, optical, acoustical or other forms of propagated signals (e.g., carrier waves, infrared signals, digital signals, etc.), and others.

In another form, a non-transitory article, such as a non-transitory computer readable medium, may be used with any of the examples mentioned above or other examples except that it does not include a transitory signal per se. It does include those elements other than a signal per se that may hold data temporarily in a "transitory" fashion such as RAM and so forth.

Examples of hardware elements may include processors, microprocessors, circuits, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), logic gates, registers, semiconductor device, chips, microchips, chip sets, and so forth. In some embodiments, the one or more processors may be implemented as a Complex Instruction Set Computer (CISC) or Reduced Instruction Set Computer (RISC) processors; x86 instruction set compatible processors, multi-core, or any other microprocessor or central processing unit (CPU). In various implementations, the one or more processors may be dual-core processor(s), dual-core mobile processor(s), and so forth.

One or more aspects of at least one embodiment may be implemented by representative instructions stored on a machine-readable medium which represents various logic within the processor, which when read by a machine causes the machine to fabricate logic to perform the techniques described herein. Such representations, known as "IP cores" may be stored on a tangible, machine readable medium and supplied to various customers or manufacturing facilities to load into the fabrication machines that actually make the logic or processor.

FIGS. 1 through 12 illustrate exemplary computer-based systems and methods providing enhanced predictive images for aesthetic medical procedures in accordance with at least some embodiments of the present disclosure. The following embodiments provide technical solutions and technical improvements that overcome technical problems, drawbacks and/or deficiencies in at least one technical field involving speed and efficiency of computing systems utilized in assisting the performance of medical treatments described herein. For example, at least one technical difficulty is the efficiency of computing system in assisting extracting from images, e.g., pixels, useful visual data that can be utilized to predict outcomes of various medical treatments described here. As explained in more detail below, the present disclosure provides a technically advantageous computer architecture that improves predictive visualization for aesthetic procedures, based at least in part on medical image data of other patients to formulate a medical procedure plan and predict a result of the medical procedure plan, thereby reducing unwanted medical procedure results. In some embodiments, the systems and methods are technologically improved by being programmed with machine-learning modeling to create a predicted post-treatment image. Some embodiments leverage the wide-spread use of mobile personal communication devices (e.g., smart phones with integrated cameras) to facilitate the inputting of user-generated data to enhance medical procedure plan. FIG. 1 illustrates a block diagram illustration of an exemplary predictive visualization system 100 consistent with some embodiments of the present disclosure. The components and arrangements shown in FIG. 1 are not intended to limit the disclosed embodiments as the components used to implement the disclosed processes and features may vary. In accordance with the disclosed embodiments, the predictive visualization system 100 may include a server 106 in communication with a first user computing device 104 and a second user computing device 108 via a network 110.

Network 110 may be of any suitable type, including individual connections via the internet such as cellular or Wi-Fi networks. In some embodiments, network 110 may connect participating devices using direct connections such as radio-frequency identification (RFID), near-field communication (NFC), Bluetooth™, low-energy Bluetooth™ (BLE), Wi-Fi™, ZigBee™ ambient backscatter communications (ABC) protocols, USB, WAN or LAN. Because the information transmitted may be personal or confidential, security concerns may dictate one or more of these types of connections be encrypted or otherwise secured. In some embodiments, however, the information being transmitted may be less personal, and therefore the network connections may be selected for convenience over security.

Server 106 may be associated with a medical institution or practice. For example, server 106 may manage patient information. One of ordinary skill will recognize that server 106 may include one or more logically or physically distinct systems.

In some embodiments, the server 106 may include hardware components such as a processor (not shown), which may execute instructions that may reside in local memory and/or transmitted remotely. In some embodiments, the processor may include any type of data processing capacity, such as a hardware logic circuit, for example, an application specific integrated circuit (ASIC) and a programmable logic, or such as a computing device, for example a microcomputer or microcontroller that includes a programmable microprocessor.

In some embodiments, the first user computing device 104 may be associated with first user who is a medical practitioner 112. In some embodiments, the second user computing device 108 may be associated with a second user who is a patient 114. When a medical treatment is being planned by the medical practitioner 112, the server 106 may prompt the patient 114 to provide user input information, such as an image and a description of the areas the patient 114 would like treated, via the second user computing device 108.

In some embodiments, the first user computing device 104 and/or the second user computing device 108 may be desktop computers. In some embodiments, the first user computing device 104 and/or the second user computing device 108 may be mobile computing devices. The first user computing device 104 and/or the second user computing device 108, or mobile user devices, may generally include at least computer-readable non-transient medium, a processing component, an Input/Output (I/O) subsystem and wireless circuitry. These components may be coupled by one or more communication buses or signal lines. The first user computing device 104 and/or the second user computing device 108 may be any portable electronic device, including a handheld computer, a tablet computer, a mobile phone, laptop computer, tablet device, a multi-function device, a portable gaming device, a vehicle display device, or the like, including a combination of two or more of these items. In some embodiments, the mobile user devices may be any appropriate device capable of taking still images or video with an equipped front camera.

As depicted in FIG. 1, in some embodiments, the first user computing device 104 includes a medical practitioner camera 116 which is used to capture input image data, or pre-treatment images. In some embodiments, the medical practitioner camera 116 may be integrated into the first user computing device 104. In some embodiments, the medical practitioner camera 116 may be an external camera that is able to transmit the pre-treatment images via a hardwired or wireless connection.

As shown in FIG. 1, in some embodiments, the second user computing device 108 includes a patient camera 120. In some embodiments, at least one patient image may be captured by the patient camera 120 and transmitted via network 110. In some embodiments, the at least one image capture may be performed by the medical treatment planning application 130 available to all users of the second user computing device 108. In some embodiments, the at least one image capture may be performed by a camera application that comes with a mobile second user computing device 108, and the resulting at least one image may be uploaded to the medical treatment planning application 130.

In some embodiments, the wireless circuitry is used to send and receive information over a wireless link or network to one or more other devices' suitable circuitry such as an antenna system, an RF transceiver, one or more amplifiers, a tuner, one or more oscillators, a digital signal processor, a CODEC chipset, memory, etc. The wireless circuitry can use various protocols, e.g., as described herein.

It should be apparent that the architecture described is only one example of an architecture for the first user computing device 104 and/or the second user computing device 108, and that the first user computing device 104 and/or the second user computing device 108 can have more or fewer components than shown, or a different configuration of components. The various components described above can be implemented in hardware, software, or a combination of both hardware and software, including one or more signal processing and/or application specific integrated circuits.

In some embodiments, the first user computing device 104 and the second user computing device 108 may include an application such as a medical treatment planning application 130 (or application software) which may include program code (or a set of instructions) that performs various operations (or methods, functions, processes, etc.), as further described herein.

Examples of software may include software components, programs, applications, computer programs, application programs, system programs, machine programs, operating system software, middleware, firmware, software modules, routines, subroutines, functions, methods, procedures, software interfaces, application program interfaces (API), instruction sets, computing code, computer code, code segments, computer code segments, words, values, symbols, or any combination thereof. Determining whether an embodiment is implemented using hardware elements and/or software elements may vary in accordance with any number of factors, such as desired computational rate, power levels, heat tolerances, processing cycle budget, input data rates, output data rates, memory resources, data bus speeds and other design or performance constraints.

In some embodiments, the medical treatment planning application 130 enables the medical practitioner 112 to access, view and/or plan a medical treatment of the patient 114. For example, in some embodiments, the medical treatment planning application 130 may allow the medical practitioner 112 to provide various inputs regarding the plan of procedure for the intended medical treatment, as discussed in further detail below. In some embodiments, the medical treatment planning application 130 enables the patient 114 to upload patient information such as an image and describe the area they want to change. The patient information may then be uploaded to the server 106, via the medical treatment planning application 130, for the medical practitioner 112 to view and create a treatment plan.

In some embodiments, the medical treatment planning application 130 enables the patient 114 to upload a medical treatment request to the server 106 for the medical practitioner 112 to access. In some embodiments, the medical treatment planning application 130 may be an application provided by the medical practitioner 112. In one implementation, the medical treatment planning application 130 may be automatically installed onto the second user computing device 108 after being downloaded. In addition, in some embodiments, the medical treatment planning application 130 or a component thereof may reside (at least partially) on a remote system (e.g., server 106) with the various components (e.g., front-end components of the medical treatment planning application 130) residing on the second user computing device 108. As further described herein, the medical treatment planning application 130 and the server 106 may perform operations (or methods, functions, processes, etc.) that may require access to one or more peripherals and/or modules. In the example of FIG. 1, the server 106 includes a predictive visualization module 138.

The predictive visualization module 138 may be implemented as an application (or set of instructions) or software/hardware combination configured to perform operations (or methods, functions, processes, etc.) for receiving and processing visual and medical treatment data inputs (e.g., without limitation, image(s), video(s), etc.), via the network 106, from the medical practitioner camera 116 of the first user computing device 104. The predictive visualization module 138 may receive pre-treatment images and a medical treatment plan inputs and employ a machine learning engine 144 to generate modified predicted images of the patient. In some embodiments the machine learning engine 144 may include, e.g., software, hardware and/or a combination thereof. For example, in some embodiments, the machine learning engine 144 may include a processor and a memory, the memory having instructions stored thereon that cause the processor to determine, without limitation, at least one predictive post-treatment image.

In some embodiments, the machine learning engine 144 may be configured to utilize a machine learning technique. In some embodiment, the machine learning engine 144 may include one or more of a neural network, such as a feedforward neural network, radial basis function network, an image classifier, recurrent neural network, convolutional network, generative adversarial network, a fully connected neural network, or some combination thereof, for example. In some embodiments, the machine learning engine 144 may be composed of a single level of linear or non-linear operations or may include multiple levels of non-linear operations. For example, the machine learning model may include numerous layers and/or hidden layers that perform calculations (e.g., dot products) using various neurons.

In some embodiments and, optionally, in combination of any embodiment described above or below, an exemplary implementation of Neural Network may be executed as follows:
i) Define Neural Network architecture/model,
ii) Transfer the input data to the exemplary neural network model,
iii) Train the exemplary model incrementally,
iv) determine the accuracy for a specific number of timesteps,
v) apply the exemplary trained model to process the newly-received input data,
vi) optionally and in parallel, continue to train the exemplary trained model with a predetermined periodicity.

In some embodiments, the machine learning engine 144 may employ Artificial Intelligence (AI)/machine learning techniques to generate modified predicted images of the patient in response to one or more medical treatments or procedures being performed. In some embodiments, the machine learning engine 144 is a convolutional neural network that performs a convolution operation to recognize objects in images. In some embodiments, a deep convolutional neural network (CNN) may be run to retrieve a feature vector, known as the encoder part. In some embodiments, patient metadata info may be connected with the feature vector and nonlinear convolutional layers are run to create a generated predictive image. In some embodiments, the generated predictive image may be a real-life simulation image that predicts the medical output approximately two weeks post-treatment. In some embodiments, the generated predictive image may be applied only to areas of the original image that were affected. In some embodiments, the convolutional neural network may be trained as described below.

In some embodiments, the machine learning engine 144 is trained on a set of pre-treatment training images and post-treatment training images of patients that had previously undergone relevant medical procedures. In some embodiments, the pre-treatment training images and post-treatment training images are collected from at least 1,000 images to receive initial results up until 100,000 images to get high accuracy. In some embodiments, the machine learning engine 144 is trained on hundreds of pre-treatment training images and post-treatment training images. In other embodiments, the machine learning engine 144 is trained on thousands of pre-treatment training images and post-treatment training images. In other embodiments, the machine learning engine 144 is trained on tens of thousands of pre-treatment training images and post-treatment training images. In other embodiments, the machine learning engine 144 is trained on hundreds of thousands of pre-treatment training images and post-treatment training images.

In some embodiments, the pre-treatment training images and post-treatment training images may be specific to a physician, a practice, a procedure, a type of product used (e.g., Restylane®), a particular part of the body, etc. In some embodiments, the pre-treatment training images and the post-treatment training images depict at least one area of a human. In some embodiments, the at least one area of a human may be, but is not limited to, a face, a cheek, a neck, etc. In some embodiments, the machine learning engine 144 is trained on unlabeled pre-treatment training images and post-treatment training images. In some embodiments, the machine learning engine 144 is trained on pre-treatment training images and post-treatment training images that include procedure planning data. For example, in some embodiments, the pre-treatment training images and/or the post-treatment training images include quadratic data such as, for example, the location of each injection point, the amount of product used and the syringe type. In some embodiments, the post-treatment training images depicts the same patient as the pre-treatment training images, with the same face orientation, two weeks post-treatment.

In some embodiments, the pre-treatment training images and the post-treatment training images are produced using a high-resolution image capture system. This high-resolution image capture system may allow for pre-treatment and post-treatment images to be taken with consistent image properties. For example, in some embodiments, the image capture system may provide consistent lighting, zoom, orientation, shading, focus, etc. In some embodiments, the images may be two-dimensional images. In other embodiments, the pre-treatment training images and/or the post-treatment training images may be three-dimensional images.

In some embodiments, a registration process may be used to finetune the alignment of the pre-treatment training images with the alignment of the post-treatment training images. In some embodiments, facial landmarks may be used to align pre-treatment training images with post-treatment training images. In some embodiments, from 10 to 500 facial landmarks may be used to align pre-treatment training images with post-treatment training images. In some embodiments, the post-treatment training images may be white balanced with the pre-treatment training images.

In some embodiments, at least one loss function may be applied to the post-treatment training images around the areas that are medically treated. In some embodiments, the loss functions that may be applied include, but are not limited to, mean square error, mean absolute error, internal adversarial networks, open source adversarial networks that predict photoshopped images, and combinations thereof.

In some embodiments, a generative adversarial network (GAN) loss function may be used to create more realistic images. Use of the GAN loss function may also minimize artifacts that might happen due to the nature of generative networks.

In some embodiments, back propagation may be used to send a post-treatment training image and/or calculated error for each output of a layer back through the layers of the machine learning model to improve the accuracy of the machine learning engine 144. For example, a predicted post-treatment image may be generated and compared to an actual post-treatment image that is obtained after the corresponding medical procedures are performed on the patient. The comparison of the actual post-treatment image and the predicted post-treatment image may cause the machine learning engine 144 to update parameters (e.g., weights, biases, etc.) to more accurately predict images. In some embodiments, facial landmarks may be used to set loss points for weights back propagation. In some embodiments, the machine learning engine 144 may use a set of data (e.g., actual post-treatment images) to improve the machine learning engine 144 at a later time (even if all data is selected from the same base data set).

In some embodiments, facial landmarks may be used to focus the machine learning loss function to look only at specific locations in an image. Thus, the background of the image and other minor differences unrelated to the plan of treatment are ignored. For example, in some embodiments, hair may be a portion of an image that is ignored while the neural network is being fine-tuned.

Figure 2:
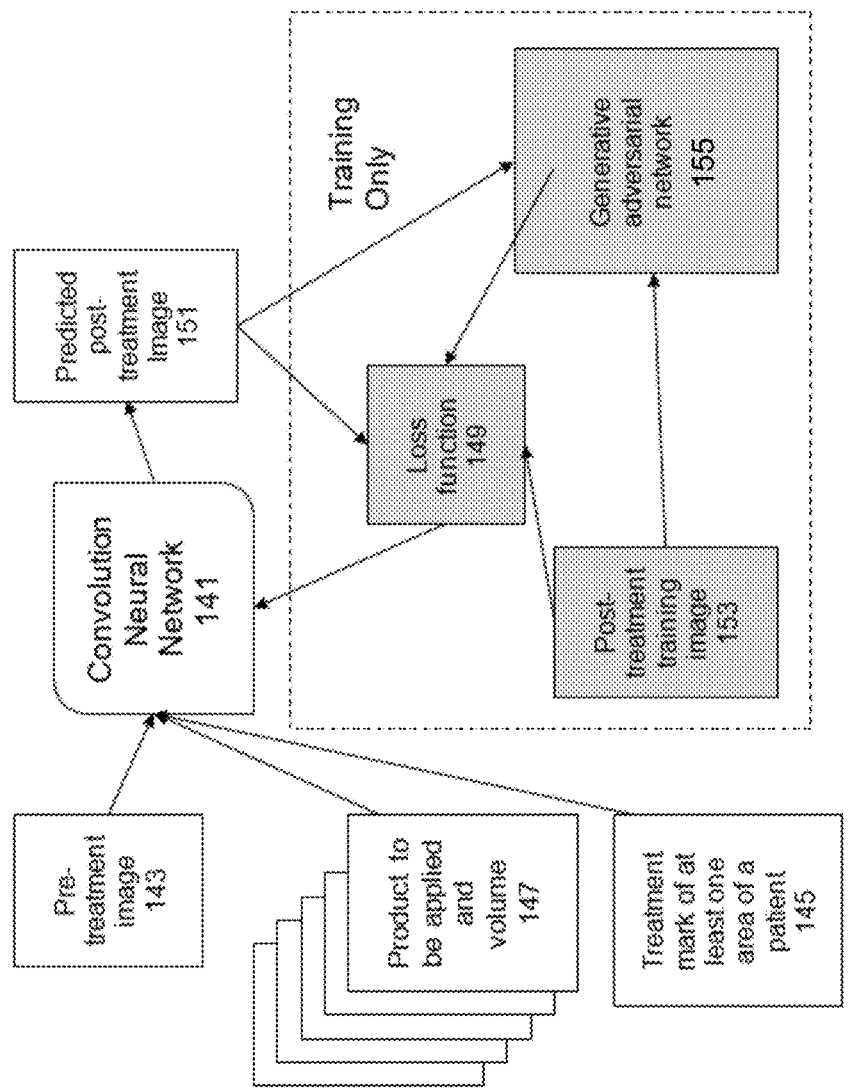
FIG. 2 is a block diagram illustrating an exemplary architecture of a machine learning engine, according to one or more embodiments of the present disclosure.

FIG. 2 depicts an exemplary structure of an inference and training scheme of the machine learning model. In some embodiments, a convolutional neural network 141 may receive three types of inputs: 1) the pre-treatment image 143; 2) a treatment mark 145 on the pre-treatment image indicating at least one area of a patient to be treated; and 3) the product to be applied and volume thereof 147. The convolutional neural network output is a predicted post-treatment image 151. In some embodiments, a lost function 149 and a generative adversarial network 155 may be applied to the predicted post-treatment image 151 and post-treatment training images 153 to minimize the differences between the before and after image only in specific locations we know are being treated. Due to multiple comparisons of the same marks indicating areas to be treated but different substances, the machine learning engine 144 may learn the effect and range of tissue behaviors post-injection per specific area.

Thus, by using the trained machine learning engine 144, the present disclosure addresses technical difficulty in the field relating to speed and efficiency of computing systems utilized in assisting the performance of medical treatments described herein.

Figure 3:
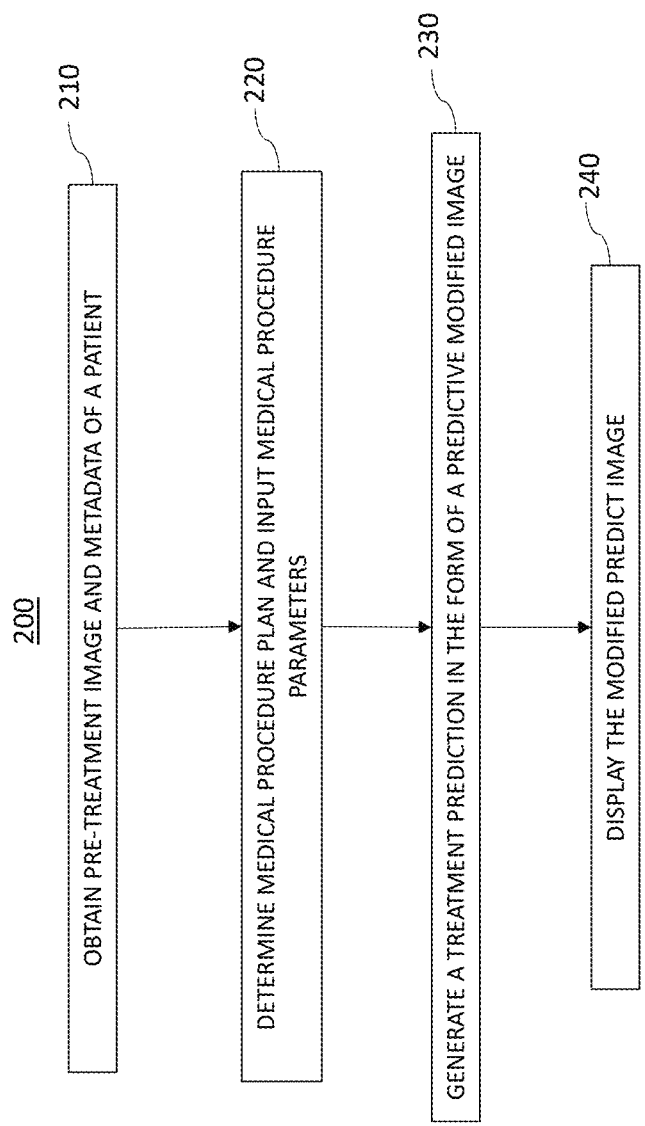
FIG. 3 is a flow diagram illustrating an example of a computer-based process for predictive visualization of a medical procedure of a patient, according to one or more embodiments of the present disclosure.

FIG. 3 is a process flow diagram illustration of an example of an illustrative process for predictive visualization for a medical procedure according to one or more embodiments of the present disclosure. The exemplary process 200 may be executed by software, hardware, or a combination thereof. For example, process 200 may be performed by including one or more components described in the predictive visualization system 100 of FIG. 1 (e.g., server 106, first user computing device 104 and second user computing device 108).

Figure 4:
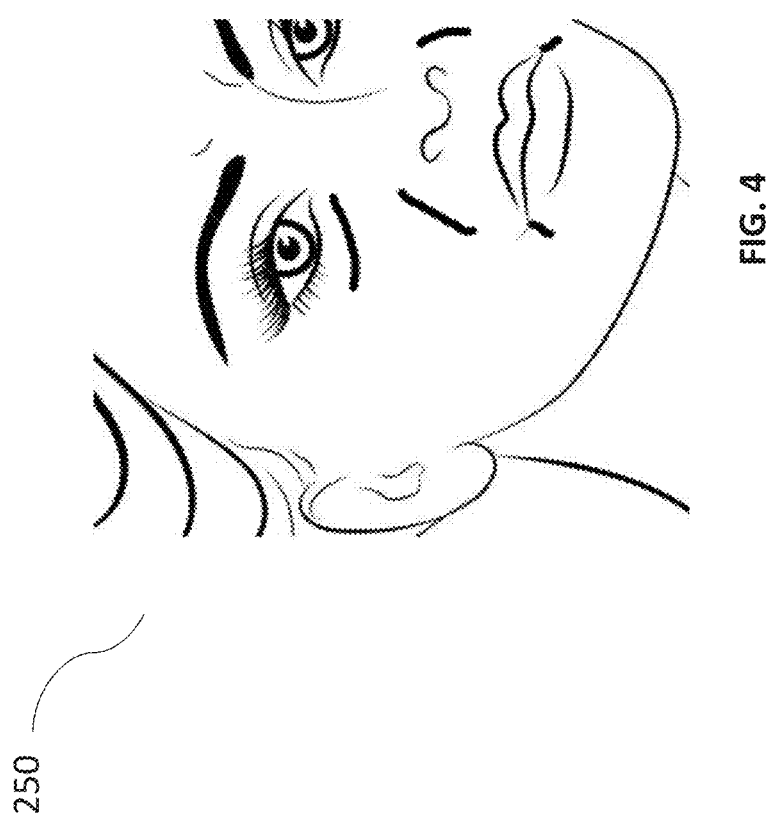
FIG. 4 is an exemplary image of a patient in a current patient state, according to one or more embodiments of the present disclosure.

In 210, the first user computing device 104 may obtain a pre-treatment image 250 of a patient. FIG. 4 depicts an exemplary pre-treatment image 250 of a patient. The pre-treatment image 250 may be taken by the camera 116 of the first user computing device 104. The pre-treatment image 250 may include a current representation of the patient 114. In some embodiments, the first user computing device 104 also receive patient metadata such as, for example, age, race and other applicable information.

Figure 5:
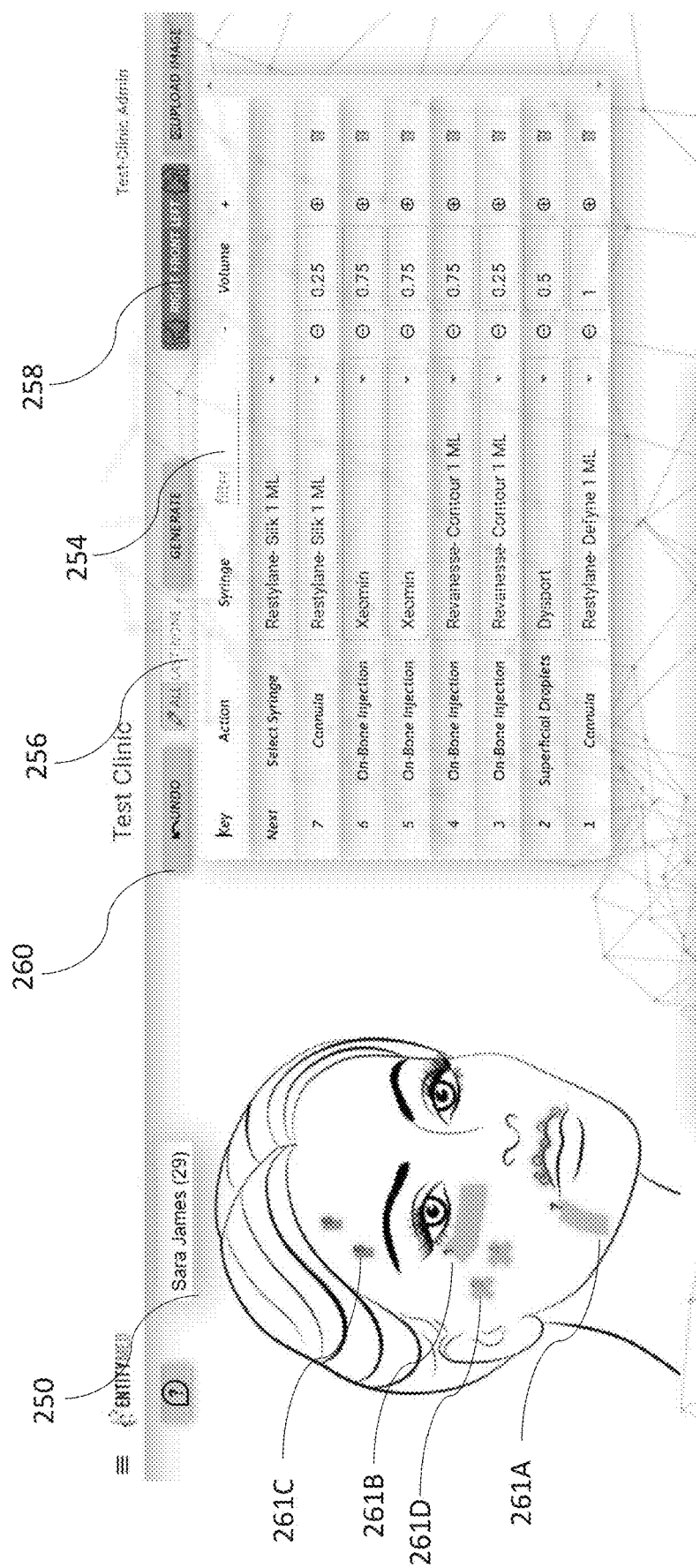
FIG. 5 is a view of an exemplary medical treatment planning application, according to one or more embodiments of the present disclosure.

In 220, the medical practitioner 112 determines a medical procedure plan and inputs parameters relating to the medical procedure plan via the medical treatment planning application 130. In some embodiments, the medical treatment planning application 130, executed on the first user computing device 104, may include a user interface 252 through which the parameters may be input. FIG. 5 depicts a user interface 252 of an exemplary medical treatment planning application 130 that enables a medical practitioner 112 to plan a medical treatment, as will be discussed in further detail below.

In some embodiments, the medical procedure is an aesthetic or cosmetic medical procedure. In some embodiments, the medical procedure is non-invasive, minimally-invasive, surgical, or a combination thereof. Exemplary medical procedures include, but are not limited to, face and chest dermatological skin enhancements including, for example, aesthetic lasers for skin modeling, face contouring, face peeling and resurfacing using either chemical or $CO_2$ lasers.

In some embodiments, the medical procedure includes administration of a therapeutic product. In some embodiments, the therapeutic product is an injection. Injections may be administered in several ways including, but not limited to, on-bone injections, cannular injections, and super-facial injections in the form of droplets. In some embodiments, the injection is a neuromodulator. In some embodiments, the neuromodulator is a nerve-inhibiting product such as, for example, Botox® and Dysport®. In some embodiments, the injection is a dermal filler such as, for example, Restylane®, Juvederm®, Belotero®, Durolane®, Sculpta®, and Kybella®, HArmoniCa®.

In some embodiments, as depicted in FIG. 5, medical treatment planning application 130 displays the pre-treatment image 250 of the patient on the user interface 252. In some embodiments, the medical treatment planning application 130 may then prompt the medical practitioner 112 to input parameters of the plan of the medical procedure. For example, in some embodiments, the medical treatment planning application 130 allows the medical practitioner 112 to position the mouse pointer over the pre-treatment image 250 to place marks 261A-261D at the areas at which a product is to be administered. In some embodiments, the medical practitioner 112 may also input the product 254 (e.g. Botox®, Restylane®, etc.), administration method 256 (i.e., type of injection) and volume 258 at each mark 261A-261D. In some embodiments, the first user interface 252 provides a table 260 to be filled out by the medical practitioner 112 for each mark placed on the pre-treatment image 250. In some embodiments, the table 260 may provide drop-down options of the name of the product and/or the volume of the product which the medical practitioner 112 may select from.

Figure 6:
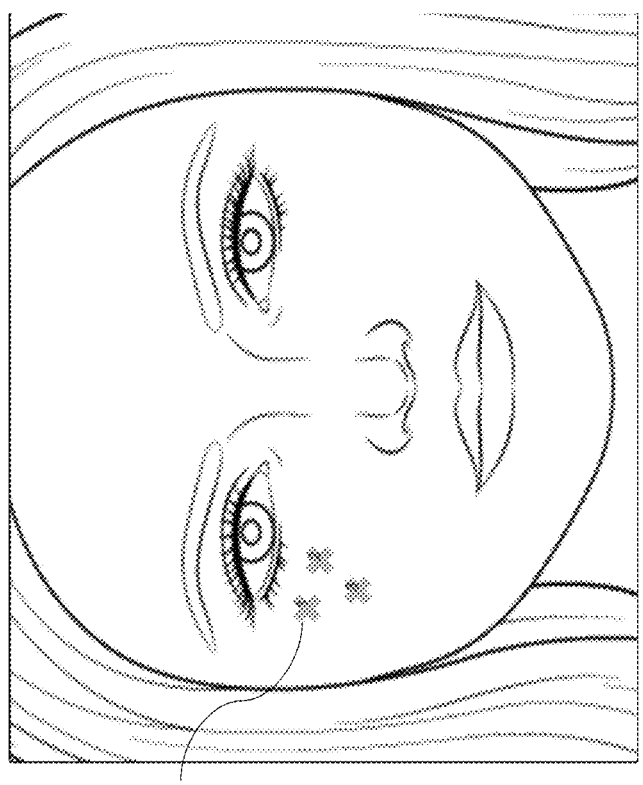
FIG. 6 is an illustration of a patient image depicting a first exemplary treatment, according to one or more embodiments of the present disclosure.
Figure 7:
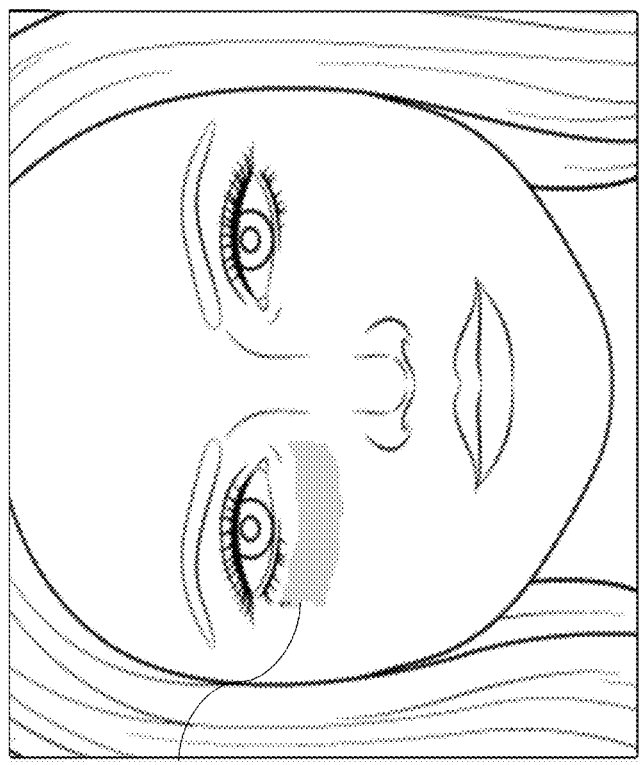
FIG. 7 is an illustration of a patient image depicting a second exemplary treatment, according to one or more embodiments of the present disclosure.
Figure 8:
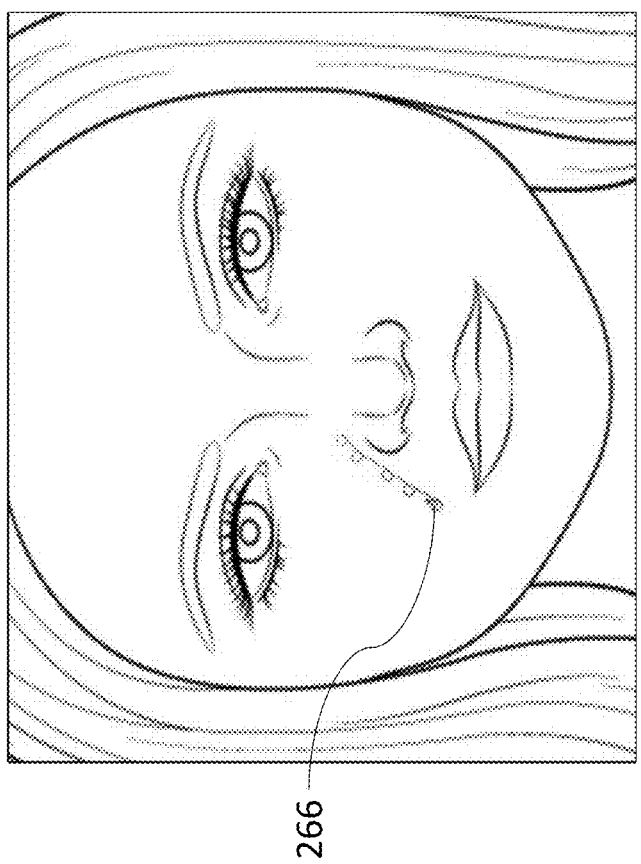
FIG. 8 is an illustration of a patient image depicting a third exemplary treatment, according to one or more embodiments of the present disclosure.

For example, in FIG. 5 mark 261A indicates where 0.25 mL Restylane is to be administered by cannula, mark 261B indicates where 1 mL Restylane-Defyne is to be administered by cannula, mark 261C indicates where 0.75 mL Xeomin is to be administered by on-bone injection and mark 261D indicates where 0.25 mL Revanesse-Contour is to be administered by on-bone injection. As depicted in FIGS. 6-8, in some embodiments, different marks indicate different types of administration method. For example, in some embodiments, the x-type marks 262 of FIG. 6 indicate an on-bone injection, the highlighted mark 264 of FIG. 7 indicates an injection using a cannula and the circular marks 266 of FIG. 8 indicate a super-facial injection in the form of droplets.

In 230, the medical treatment planning application 130 is instructed by the medical practitioner 112 to generate a treatment prediction in the form of a predictive modified image 268 of the patient. In some embodiments, the first user interface 252 of the predictive visualization system 100 may include a "Generate" button which starts the AI algorithm of the machine learning engine 144. Specifically, in some embodiments, the machine learning engine 144 may be used by the predictive visualization module 138 to apply the AI techniques discussed above to generate the modified predictive image 268 of the patient 114 that may result from performing the one or more selected medical treatments on the patient 114.

Figure 9:
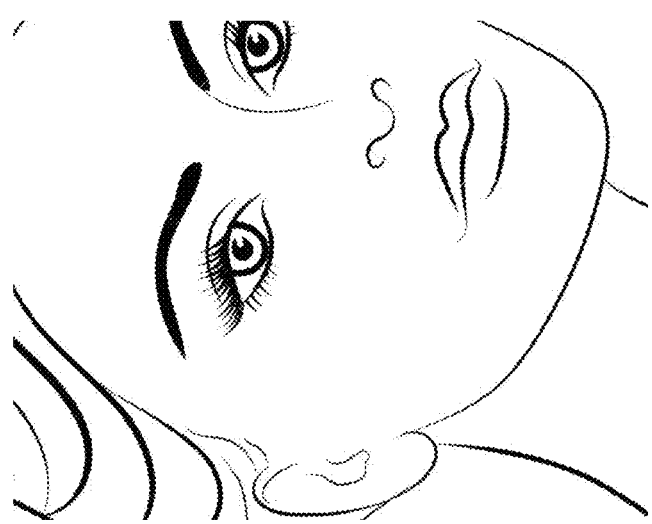
FIG. 9 is an exemplary predictive image output by the medical treatment planning application, according to one or more embodiments of the present disclosure.

In 240, the modified predictive image 268 is displayed on the first user computing device 104 via the medical treatment planning application 130. FIG. 9 is an exemplary modified predictive image 268 generated by the predictive visualization module 138 in response to the inputs to the pre-treatment image 250 provided by the medical practitioner 112 for a medical procedure.

Figure 10:
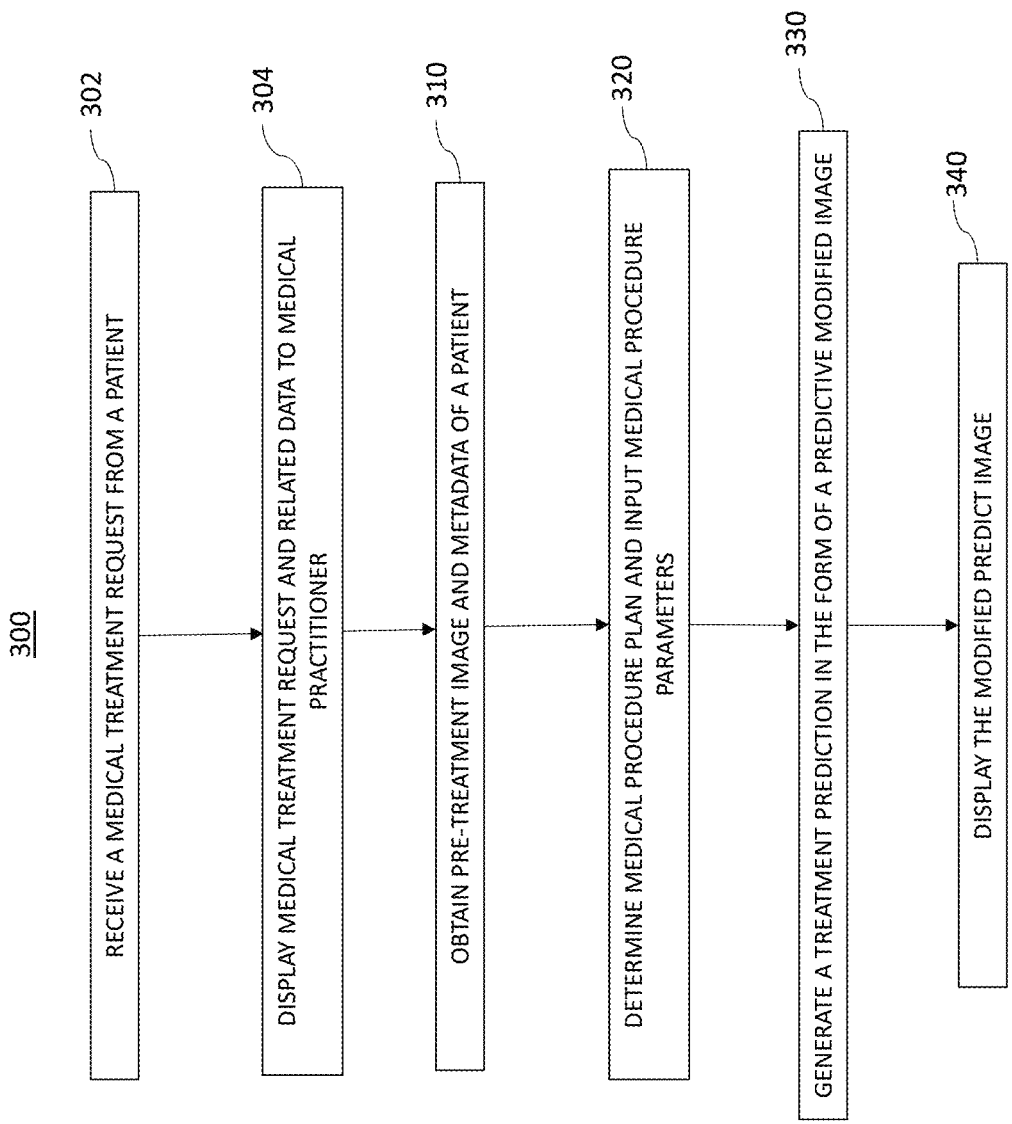
FIG. 10 is a flow diagram illustrating an example of a computer-based process for predictive visualization of a medical procedure of a patient, according to one or more embodiments of the present disclosure.

FIG. 10 is a process flow diagram illustrating an example of an illustrative process for predictive visualization for a medical procedure according to one or more embodiments of the present disclosure. The exemplary computer-mediated process 300 may be executed by software, hardware or a combination thereof. For example, process 300 may be performed by including one or more components described in the predictive visualization system 100 of FIG. 1 (e.g., server 106, first user computing device 104 and second user computing device 108).

In some embodiments, the process 300 may include the steps of as the process 200 and may further include steps in which a patient may provide a medical treatment request to the medical practitioner via the medical treatment planning application 130. Specifically, steps 310-340, as shown in FIG. 11, correspond to steps 210-240.

Figure 12:
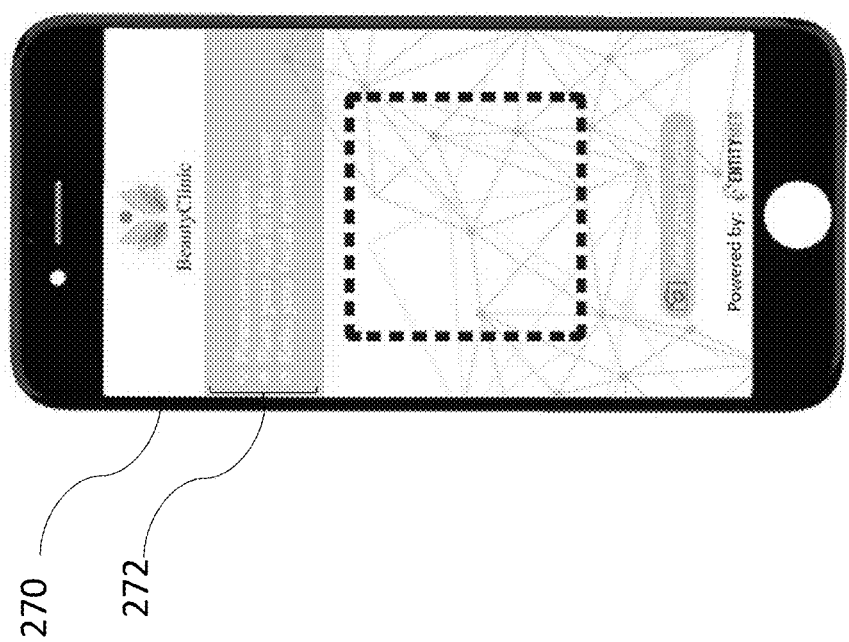
FIG. 12 is another view of the exemplary medical treatment planning application of FIG. 10, according to one or more embodiments of the present disclosure.
Figure 13:
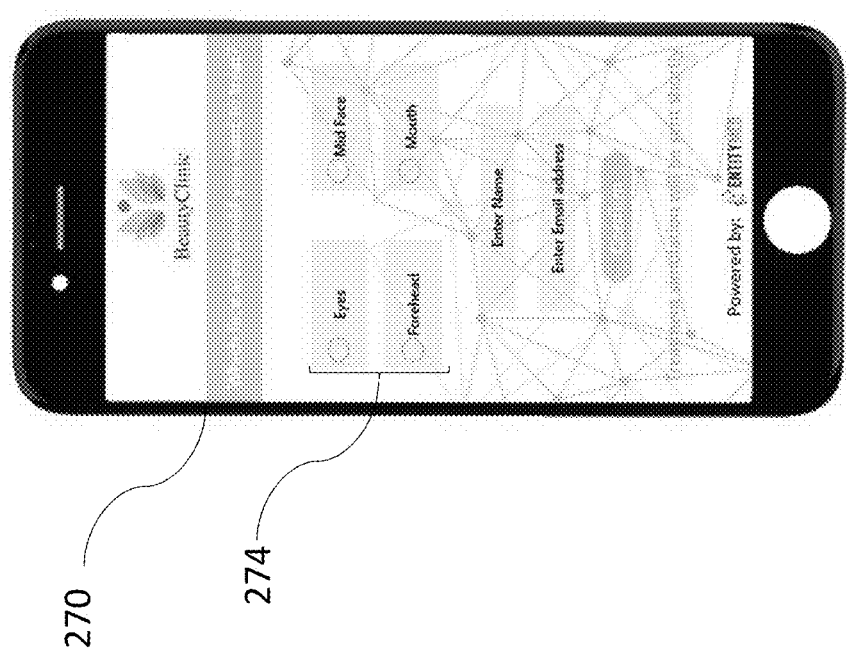
FIG. 13 is another view of the exemplary medical treatment planning application of FIG. 10, according to one or more embodiments of the present disclosure.

In 302, the server 106 may receive a medical treatment request from the patient 114. In some embodiments, the patient may provide the medical treatment request via the medical treatment planning application 130 executed by the second user computing device 108. In some embodiments, the medical treatment request may include visual data such as, for example, a photograph or a video of the patient 114 and a description of the area that the patient 114 would like to be treated. FIGS. 11-13 depict an exemplary second user interface 270 of the medical treatment planning application 130 executed on the second user computing device 108.

In some embodiments, the camera 120 of the second user computing device 108 is used by the patient 114 to capture visual data of a patient 114. In some embodiments, the camera 120 may be a camera sensor-type imaging device or the like (e.g., a complementary metal oxide-semiconductor-type image sensor (CMOS) or a charge-coupled device-type image sensor (CCD)), without the use of a red-green-blue (RGB) depth camera and/or microphone-array to locate who is speaking. In some embodiments, an RGB depth camera and/or microphone-array might be used in addition to or as an alternative to the camera sensor. In some examples, the camera 120 may be provided via either a peripheral eye tracking camera or as an integrated a peripheral eye tracking camera in environment 100.

Figure 11:
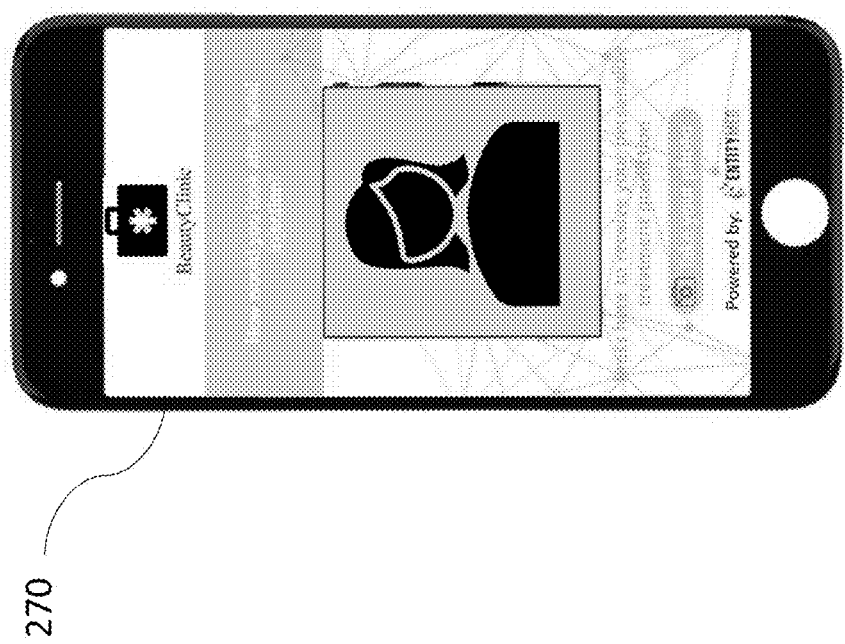
FIG. 11 is a view of an exemplary medical treatment planning application, according to one or more embodiments of the present disclosure.

FIG. 11 depicts an initial display of the medical treatment planning application 130, executed by the second user computing device 108, prompting the patient 114 to take a patient image, according to some embodiments of the present disclosure. In some embodiments, if the patient 114 selects "Take your photo", the medical treatment planning application 130 provides on-screen guide indicators 272 to the patient 114, instructing the patient 114 how to take a photograph of their current state, as depicted in FIG. 12. Once a photo is captured by the camera 120 of the second user computing device 108, in some embodiments, the patient 114 is then able to indicate which areas 274 he/she would like to treat, as depicted in FIG. 13.

At step 304, the medical treatment request, including the visual data and description of areas to be treated is displayed to the medical practitioner 112 via the medical treatment planning application 130 executed on the first user computing device 104.

The disclosure of this application has been described above both generically and with regard to specific embodiments. It will be apparent to those skilled in the art that various modifications and variations can be made in the embodiments without departing from the scope of the disclosure. Thus, it is intended that the embodiments cover the modifications and variations of this invention provided they come within the scope of the appended claims and their equivalents.

What is claimed is:

1. A method comprising:
    training, by a processor, a predictive visualization machine learning model to generate predicted post-treatment images to obtain a trained predictive visualization machine learning model, based at least in part on:
        a) a set of pre-treatment training images of at least one area of a human;
        b) a plan of treatment related to the set of pre-treatment training images; and
        c) a set of post-treatment training images of the at least one area of the human related to the set of pre-treatment training images and the plan of treatment;
        wherein the plan of treatment comprises:
            a) at least one first treatment mark identifying where a product is to be applied on a pre-treatment image,
            b) a first product to be applied at the at least one first treatment mark, and
            c) a first volume of the product to be applied at the at least one first treatment mark;
    applying, by the processor, the trained predictive visualization machine learning model to at least one new pre-treatment image, based at least in part on a new plan of treatment comprising:
        a) at least one second treatment mark on a new pre-treatment image of the at least one area of a patient,
        b) a second product to be applied at the at least one second treatment mark, and
        c) a second volume of the second product to be applied at the at least one second treatment mark;
    generating, by the processor, at least one predicted post-treatment image via the trained predictive visualization machine learning model;
        wherein the at least one predicted post-treatment image identifies at least one modified area; and
    instructing, by the processor, to display the at least one predicted post-treatment image on a screen.

2. The method of claim 1, further comprising:
    receiving, by the processor, from the patient:
        a) at least one patient image; and
        b) at least one patient treatment request;
    wherein the new plan of treatment is based at least in part on the at least one patient image and the at least one patient treatment request.

3. The method of claim 1, wherein the predictive visualization machine learning model includes one or more of a neural network, a radial basis function network, an image classifier, a recurrent neural network, a convolutional network, a generative adversarial network, a fully connected neural network, a feedforward neural network, or a combination thereof.

4. The method of claim 1, wherein the predictive visualization machine learning model applies at least one loss function to the set of post-treatment training images.

5. The method of claim 4, wherein the at least one loss function comprises a mean square error loss function, an internal adversarial network, an opensource adversarial network, or a combination thereof.

6. The method of claim 1, wherein the first product comprises at least one of a prescription injection or a dermal filler.

7. The method of claim 1, wherein the second product and the first product are the same.

8. The method of claim 1, wherein the predictive visualization machine learning model is trained on thousands of pre-treatment training images and post-treatment training images.

9. The method of claim 1, further comprising applying, by the processor, a registration process to finetune an alignment of the set of pre-treatment training images with an alignment of the set of post-treatment training images.

10. The method of claim 9, wherein the registration process identifies from 10 to 500 facial landmarks on the set of pre-treatment training images and the set of post-treatment training images.

\* \* \* \* \*